United States Patent [19]
Brizzolara et al.

[11] Patent Number: 5,622,498
[45] Date of Patent: *Apr. 22, 1997

[54] METHOD FOR THE TREATMENT OF PERIODONTAL DISEASE BY SUSTAINED DELIVERY OF A THERAPEUTIC AGENT TO THE PERIODONTAL POCKET, COMPOSITION OF MATTER THEREFOR AND APPARATUS FOR THE ADMINISTRATION THEREOF

[75] Inventors: Nancy S. Brizzolara, Congers; Michael G. Lanzilotti, Pearl River; James R. Lawter, Goshen, all of N.Y.

[73] Assignee: American Cyanamid Company, Madison, N.J.

[ * ] Notice: The term of this patent shall not extend beyond the expiration date of Pat. No. 5,236,355.

[21] Appl. No.: 7,753

[22] Filed: Jan. 22, 1993

Related U.S. Application Data

[60] Continuation of Ser. No. 593,125, Oct. 5, 1990, Pat. No. 5,236,355, which is a division of Ser. No. 289,076, Dec. 22, 1988, abandoned.

[51] Int. Cl.⁶ .............. A61C 17/02; A61C 5/04; A61M 5/00
[52] U.S. Cl. .............. 433/80; 433/89; 604/187
[58] Field of Search .............. 433/80, 89, 90; 604/181, 187, 189, 199

[56] References Cited

U.S. PATENT DOCUMENTS

| | | |
|---|---|---|
| 3,760,503 | 9/1973 | Baskas . |
| 3,939,834 | 2/1976 | McMahon ............... 128/272 |
| 4,276,880 | 7/1981 | Malmin ............... 128/221 |
| 4,622,244 | 11/1986 | Lapka et al. ............... 427/213.32 |
| 4,685,883 | 8/1987 | Jernberg ............... 433/215 |
| 4,764,377 | 8/1988 | Goodson ............... 424/435 |
| 4,798,596 | 1/1989 | Mühlbauer ............... 604/218 |
| 4,863,072 | 9/1989 | Perler ............... 222/390 |
| 5,236,355 | 8/1993 | Brizzolara et al. ............... 433/80 |

Primary Examiner—Cary E. O'Connor
Attorney, Agent, or Firm—Hedman, Gibson & Costigan, P.C.

[57] ABSTRACT

Oral compositions for the local administration of a therapeutic agent to a periodontal pocket of a patient for alleviating dental disease comprise a plurality of dry, discrete microparticles each of which comprise an effective amount of at least one therapeutic agent dispersed in a matrix comprising a biocompatible and biodegradable polymer. Apparatus and methods are also provided for the dispensing of the dry microparticles to the periodontal pocket whereby they become tacky and adhere to the involved tissue so as to induce long term therapeutic benefits.

31 Claims, 4 Drawing Sheets

VIEW A-A

METHOD FOR THE TREATMENT OF PERIODONTAL DISEASE BY SUSTAINED DELIVERY OF A THERAPEUTIC AGENT TO THE PERIODONTAL POCKET, COMPOSITION OF MATTER THEREFOR AND APPARATUS FOR THE ADMINISTRATION THEREOF

This is a continuation of application Ser. No. 07/593,125, filed Oct. 5, 1990, now U.S. Pat. No. 3,236,355, which is a divisional of Ser. No. 07/289,076, filed Dec. 22, 1988, now abandoned.

FIELD OF THE INVENTION

This invention relates to a composition for treating dental diseases. It also relates to a process for administering said composition for the treatment of dental diseases and an apparatus to administer such compositions. More specifically, it is concerned with the method of local administration of a sustained release formulation comprising antibiotics, nonsteroidal anti-inflammatory agents, tissue growth factors and the like, or any combinations thereof, to the space surrounding the tooth which forms when the gums retract from the teeth, as in periodontal disease. When the formulation is administered to this space, called the periodontal pocket, the compositions are able to provide drug delivery to the pocket, tissues surrouding the pocket onto the oral cavity for periods of up to two weeks, and more.

BACKGROUND OF THE INVENTION

Improved methods for providing compositions for controlled release of therapeutic agents are disclosed and exemplified in applicants' above-mentioned parent application Ser. No. 07/054,372. It has now been discovered that such novel compositions are uniquely suitable for treating dental diseases.

Drugs are conventionally administered orally or via injection, often at a site remote from the target. Over a relatively short period of time, the drug diffuses into the circulatory system of the patient and is distributed to the various organs and tissues, at least one of which is the intended target for the drug. The action of the drug on organs other than the target may result in undesirable side effects. Finally, the drug is metabolized or otherwise reversibly removed from the organism by excretion or chemical deactivation. When drugs are delivered orally or by injection by conventional non-sustained release formulations, the level and duration of availability of the drug cannot be controlled independently; only the size and frequency of the dose can be manipulated. Typically, there is an initially high concentration of available drug at the site of injection or in the circulatory system which then decreases gradually as the drug is distributed and consumed within the body of the patient.

In controlled or sustained delivery, a formulation of drug and a carrier is generally administered to the patient by ingestion or implantation. The carrier forms a drug reservoir that protects the stored drug from extraneous removal mechanisms and releases the drug to the biological reservoir at a predetermined rate. Controlled, sustained delivery of a drug prevents undesirable peaking of blood levels and makes the drug available at an optimum and substantially uniform concentration over an extended period of time. Only the released drug is subject to removal via metabolism and excretion. In the controlled sustained delivery method, there is potential for control of the drug release rate by factors inherent in the delivery package itself. Some of these inherent factors, such as the rate of hydrolysis of an absorbable polymer, or the rate of transdermal diffusion are in contrast to the externalized controls associated with classical delivery methods, e.g., rate of tablet intake, frequency of injections, etc. In accordance with prior methods, the maintanance of therapeutic blood levels of an antibiotic, for example, requires a fairly precise dosing of tablets. Though this may be uncomplicated for many adults, it may be difficult where gastric problems are present or for infants, the very infirm, or in veterinary work, such as with range animals.

Although the following discussion will emphasize the treatment of periodontal disease, the invention in its broadest aspects contemplates a system to treat abnormalities of the oral cavity amenable to administration of therapeutic agents generally. Such agents comprise, by way of illustration, antifungal agents, antibacterial agents, antibiotics, anti-inflammatory agents, immunosuppressive agents, immunostimulatory agents, dentinal densitizers, odor masking agents, immune reagents, anesthetics, antiseptics, nutritional agents, antioxidants, lipopolysaccharide complexing agents, peroxides, tissue growth factors, a mixture of any of the foregoing, and the like.

Periodontal disease is an all-inclusive term for a variety of clinical conditions that are forms of either gingivitis or periodontitis. Gingivitis is an inflammation of the gingiva (or gums) that can be associated with poor oral hygiene and/or the hormonal state of the patient. It is believed that gingivitis, if untreated, will develop into periodontitis. Periodontitis is a bacterial disease in which the infection has progressed to involve the oral tissues which retain the teeth in the jawbone. Periodontitis, if untreated, will eventually result in the loss of the affected teeth.

Although dental caries may be effectively treated with a combination of proper hygiene and fluoride, periodontal disease is often more refractile to treatment. This difference in amenability to treatment reflects the markedly different environments of the oral and periodontal cavities. The oral cavity is essentially an aerobic environment, which is constantly perfused by saliva. In contrast, the periodontal microenvironment is more anaerobic and is perfused by a plasma filtrate, known as the "crevicular fluid." The growth of microorganisms within this microenvironment may cause periodontal disease. Hence, the treatment of the disease is directed toward controlling this growth. As the periodontal disease becomes more established, the periodontal microenvironment becomes more anaerobic and the flow of crevicular fluid increases.

Efforts to treat periodontal disease have been impeded by several factors. Because the site of the bacterial infection is largely inaccessible to agents present in the oral cavity, antimicrobial agents provided to the oral cavity such as, for example, in a mouth wash are generally ineffective. The increased outward flow of crevicular fluid, which accompanies periodontal disease, has the effect of preventing therapeutic agents placed within the oral cavity from entering the periodontal pocket.

Ngai et al., U.S. Pat. No. 4,250,163 disclose a method of administering a broad range of medications to the oral cavity by means of a water-swellable and mucosa-adhesive polymeric matrix, which can be in the form of a tablet, powder or granules, and which is effective for times on the order of a few hours. These treatments are normally effective for periods of hours rather than days, and a course of treatment lasting one month would require the use of numerous tablets.

Furthermore, this system is inappropriate for the treatment of periodontal disease because the drug is released into the saliva or oral mucosa, and does not penetrate the periodontal pocket to any significant extent. Buccal tapes, strips and similar disease forms suffer from the same disadvantages of inefficient delivery to the affected tissue.

Another disadvantage of such methods of dispensing drugs is that they may slip or be dislodged by the tongue or teeth, may be uncomfortable, and may interfere with the normal oral functions.

Oral systemic administration of antibiotics has been shown to be a useful method of controlling the subgingival flora. However, because of side effects such as those of the digestive system, for example pseudomembraneous colitis, anorexia, nausea and diarrhea, biochemical abnormalities such as thrombocytopenia and eosinophilia. Oral systematic administration has had only limited use in treating periodontal disease. Oral systemic therapy required frequent dosing, so patient compliance is frequently a problem.

Recent developments in the art are directed toward delivering the therapeutic agent directly to the periodontal pocket, in some cases in a controlled release formulation. In general, administration of agents directly to the pocket permits higher local drug concentrations than can be achieved by systematic administration. Doses in the latter case are limited by systematic side effects. Also some agents, such as tissue growth factors must be administered directly to the target site, i.e. the periodontal pocket.

Goodson, U.S. Pat. No. 4,175,326, describes the use of a drug-filled polymer hollow fiber. This delivery system is tied around a tooth and gently pressed below the margin of the gingiva so that it resides in the periodontal pocket, and is capable of delivering an effective dose of 2.5 micrograms of tetracycline per day per periodontal pocket for a prolonged period of a week or more.

It has been reported that tetracycline can be incorporated in polymethyl methacrylate or ethylene vinyl acetate to prepare a solid composition in the form of strips or fibers to be used for topical application to a lesion in the oral cavity, such as periodontal pockets (J. Periodontol., 53(11), 693–699 (1982) and 54(10), 575–579 (1983)).

An acrylic strip, formed from ethyl cellulose impregnated with metronidazole, is disclosed by Loesche in U.S. Pat. No. 4,568,538.

Another strip, employing a water soluble polymer of a particular elasticity and viscosity, is disclosed by Suzuki et al. in U.S. Pat. No. 4,569,837.

Although these devices may be able to dispense an appropriate drug for a time span of a week or more, they are inappropriate to widespread use because they are difficult and time consuming to apply and may be dislodged by the patient during normal oral functions.

Baker, European Patent Application No. 0244118, describes therapeutic agent containing microparticles suspended in a liquid carrier, but when put into the periodontal pocket they are prone to wash out since they do not adhere to the involved tissue.

Hasegawa et al., U.S. Pat. No. 4,701,320, disclose a stable minocycline containing gel composition for treating periodontal diseases by direct application. The compositions of Hasegawa et al. reduce bacteria in the periodontal pocket within one day of treatment, but then after one week the bacterial count increases substantially indicating a short term effect.

On the other hand, the formulation discovered by the applicants, and the subject matter of this invention, has been specifically developed to deliver therapeutic agents, e.g., minocycline, doxycycline, and continuously for periods up to two weeks, thereby providing therapeutically effective drug levels over a substantially longer period of time than taught by Hasegawa et al., and without the manipulative drawbacks of the fibers, and polymer strips.

In the above-mentioned copending applications of two of the three applicants herein, a phase separation process is used to microencapsulate therapeutic agents in a biodegradable polymer matrix, the resulting product comprising microparticles of the agent in the polymer. The microparticles described in the copending application comprise a sustained release delivery system for systemic administration to patients in need of treatment.

It has now been found that with optional modifications, such compositions are particularly useful for local administration to the periodontal pocket for treating dental diseases. The formulation of this invention is adapted to be administered as a dry powder which absorbs water upon administration and becomes tacky. This promotes adhesion to the tissues forming the periodontal pocket. Thus, no additional means to promote adhesion in the periodontal pocket are necessary with this invention. Inactive components are polymers which biodegrade and do not require removal from the crevicular pocket. Degradation products of the preferred polymers are acidic and are capable of providing the optimum pH inside the microparticles for stability of antibiotics certain tetracyclines, such as minocycline, doxycycline, and the like. As will be shown, the formulations of this invention provide drug levels in crevicular fluid for a longer period of time than, for example, gel type formulations of Hasegawa et al.

BRIEF DESCRIPTION OF THE DRAWINGS

The invention may be more readily understood by reference to the drawings in which.

SUMMARY OF THE INVENTION

Figure 1:
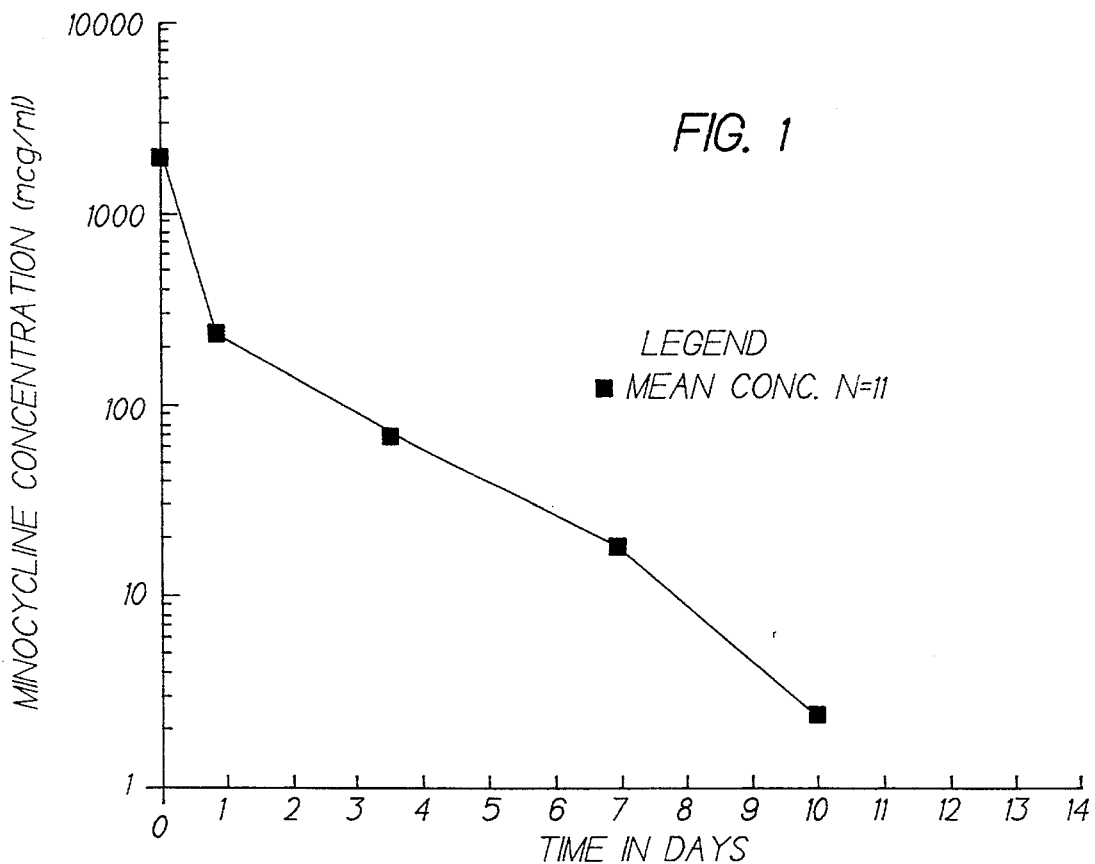
FIG. 1 is a graph illustrating minocycline concentration in crevicular fluid after administration and release from microparticles of Example 1 of this invention over a 10-day period.
Figure 2:
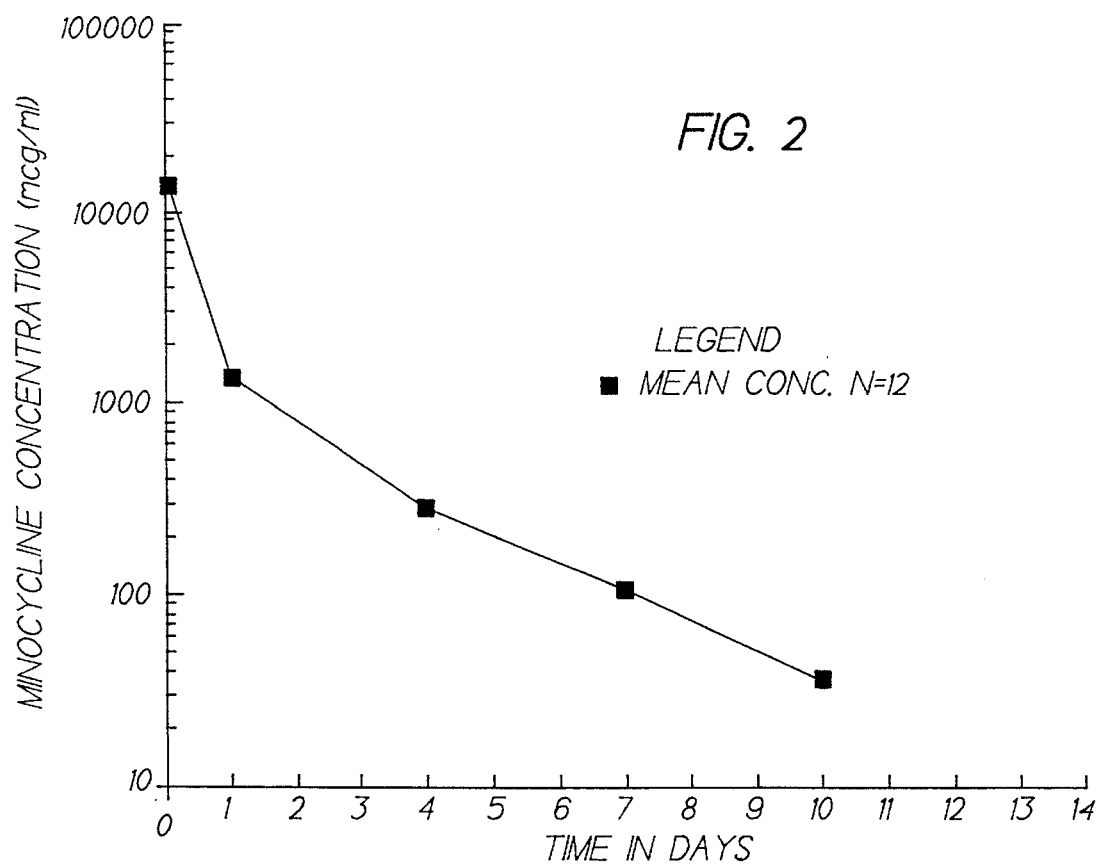
FIG. 2 is a graph illustrating minocycline concentration in crevicular fluid after administration and release from microparticles of Example 2 of this invention over a 10-day period.
Figure 3:
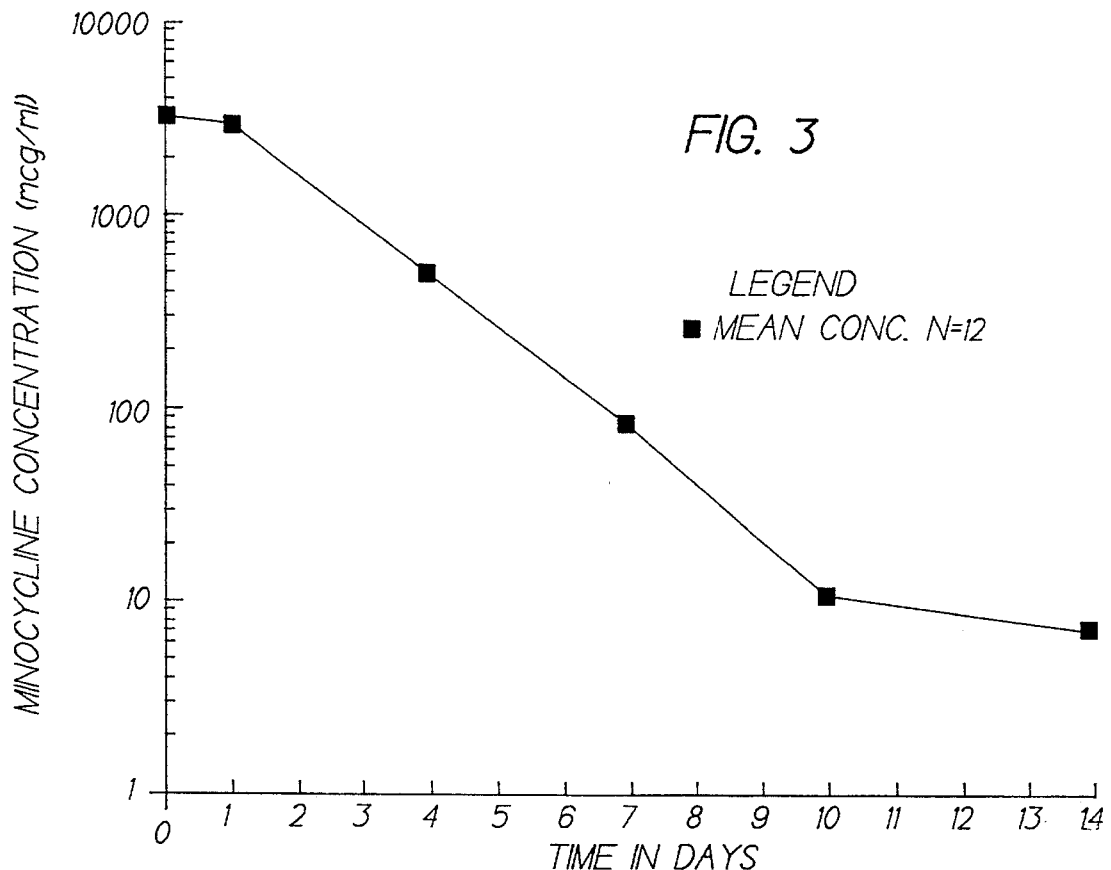
FIG. 3 is a graph illustrating minocycline concentration in crevicular fluid after administration and release from microparticles of Example 3 of this invention over a 14-day period.
Figure 4:
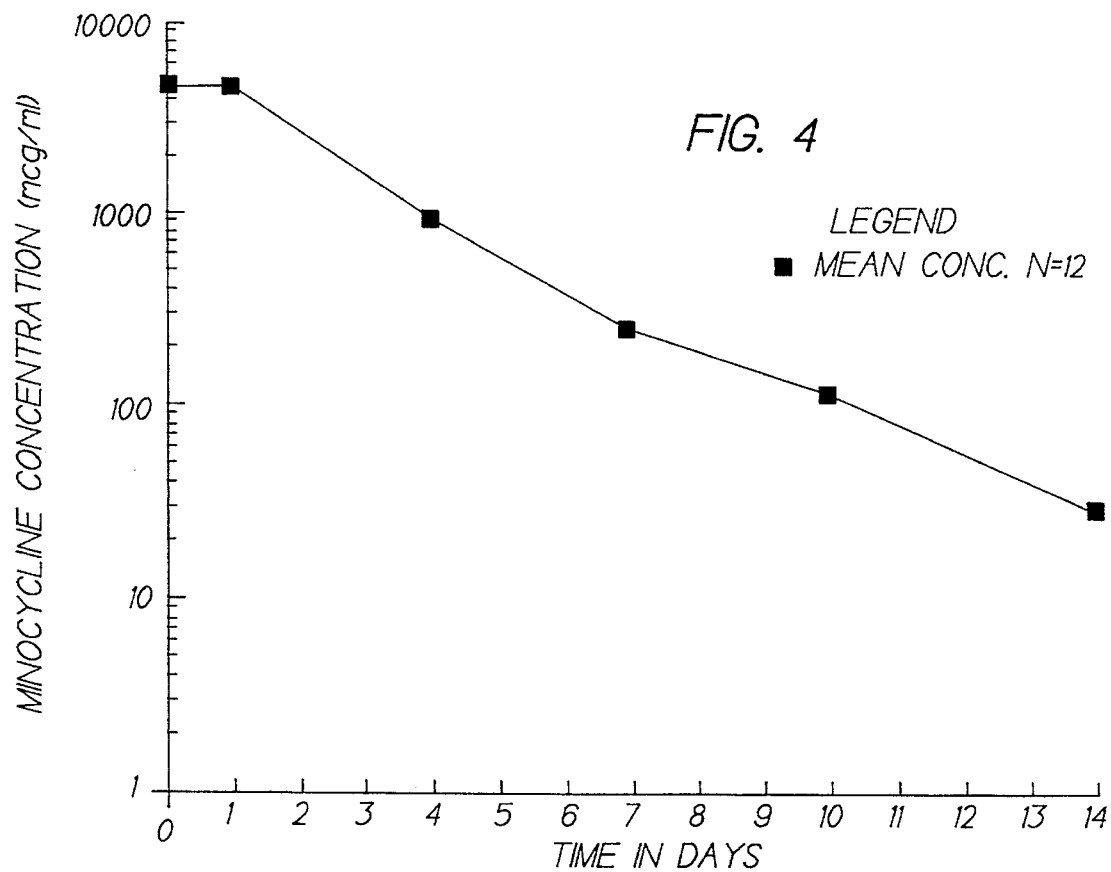
FIG. 4 is a graph illustrating minocycline concentration in crevicular fluid after administration and release from microparticles of Example 4 of this invention over a 14-day period.
Figure 5:
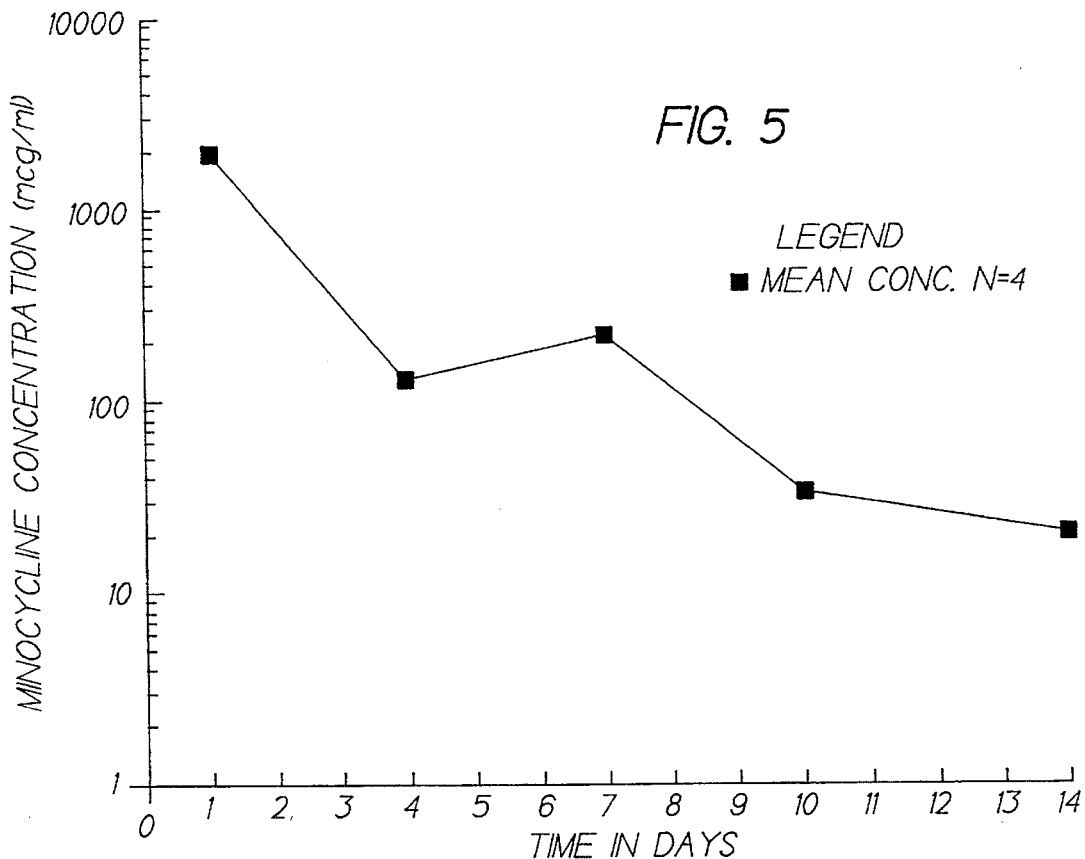
FIG. 5 is a graph illustrating minocycline concentration in crevicular fluid after a second treatment with encapsulated minocycline microparticles of Example 4, as in FIG. 4, showing retention of therapeutic levels over a 14-day period.

According to the present invention there are provided sustained release compositions for the local administration of a therapeutic agent to the periodontal pocket, said composition adapted to be administered as a plurality of dry, discrete microparticles, the composition comprising microparticles comprised of:

(i) an effective amount of at least one therapeutic agent dispersed in (ii) a matrix comprising a biocompatible and biodegradable polymer.

The invention includes an apparatus for dispensing said oral composition for alleviating dental diseases by local administration to the periodontal pocket of a patient in need of such treatment, said apparatus comprising:

(1) a container ending in an outlet means adapted to fit into the periodontal pocket between the patient's gum and teeth;

(2) means to translate an externally applied force onto said microparticles contained within the outlet means so as to dispense them through said outlet means into said periodontal pocket; and, in said outlet means, (3) a plurality of dry, therapeutic agent-containing microparticles as defined above.

The microencapsulated compositions contemplated by the present invention may be prepared by any of several techniques known in the art of microencapsulation including phase separation, coacervation, solvent evaporation, spray drying and the like. In a preferred aspect, the compositions are produced by a phase separation process which employs volatile silicone fluids as hardening agents. The resulting sustained release compositions comprise microcapsules, microparticles and microspheres, and they, typically, have an aspect ratio of less than about 3.

Further contemplated herein is a method for alleviating dental diseases comprising local administration to the space between the teeth and gum of a subject in need of such treatment, an effective amount of a plurality of dry, discrete microparticles containing therapeutic agents disperesed in a matrix comprising a biocompatible and biodegradable polymer, said microparticles being typically in the size range of about 0.1 to about 1000 microns, preferably from about 10 to about 200 and more preferably from about 30 to about 120 microns in diameter.

In general, the microcapsules are comprised of from about 0.00001 to about 50 parts by weight of therapeutic agent and is further comprised of from about 50 to about 99.99999 parts by weight of matrix. The preferred ranges are from 1 to 50, 5 to 40, and 20 to 30 parts by weight of therapeutic agent, the balance comprised of matrix. The lower ranges are suitable when the therapeutic agent is e.g., a tissue growth factor.

DETAILED DESCRIPTION OF THE INVENTION

In general, the classes of therapeutic agents which can be administered by this invention include those described hereinafter. Specific agents include those described hereinafter.

Although broadly applicable to the therapeutic agents described above, preferred are tetracycline compounds in general, and special mention for purposes of this invention is made of the use of members of the tetracycline family comprising substituted 4-, 7-, and 9-aminotetracyclines which may be represented by the following general formula:

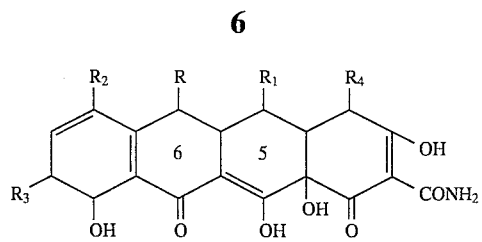

where R is hydrogen or methyl, $R_1$ is hydrogen or hydroxyl, and $R_2$, $R_3$ and $R_4$ are hydrogen, mono (lower alkyl)amino or di(lower alkyl)amino with the proviso that $R_2$, $R_3$ and $R_4$ cannot all be hydrogen. Typical compounds represented by the above general formula are, for example, 7-methylamino-6-deoxy-6-demethyltetracycline, 7-ethylamino-6-deoxy-6-demethyltetracycline, 7-isopropylamino-6-deoxy-6-demethyltetracycline, 9-methylamino-6-deoxy-6-demethyltetracycline, 9-ethylamino-6-deoxy-6-demethyltetracycline, 9-isopropylamino-6-deoxy-6-demethyltetracycline, 7,9-di(ethylamino)-6-deoxy-6-demethyltetracycline, 7-dimethylamino-6-deoxy-6-demethyltetracycline, 9-dimethylamino-6-deoxy-6-demethyltetracycline, 7-methylamino-6-deoxytetracycline, 9-ethylamino-6-deoxytetracyline, 7,9-di(methylamino)-6-deoxytetracycline, 7-diethylamino-6-deoxytetracyline, 9-diethylamino-6-deoxytetracyline, 7,9-di(methylamino)-6-deoxytetracycline, 7-methylamino--9-ethylamino-6-deoxytetracycline, and 9-methylamino-5-hydroxy-6-deoxytetracycline.

Preferred members of this family comprise tetracycline compounds selected from (a) 7-dimethylamino-6-deoxy-6-demethyltetracycline;

(b) 7-methylamino-6-deoxy-6-dimethyltetracycline;

(c) 9-methylamino-6-deoxy-6-demethyltetracycline;

(d) 7-ethylamino-6-deoxy-6-demethyltetracycline;

(e) 7-isopropylamino-6-deoxy-6-demethyltetracycline;

(f) 6-deoxy-5-oxytetracycline (g) a non-toxic acid addition salt or hydrate of (a)–(f), inclusive or (h) a mixture of any of the foregoing.

Special mention is made of the tetracycline compounds, 7-dimethylamino-6-deoxy-6-demethyltetracycline, 6-deoxy-5-oxytetracycline and their non-toxic acid addition salts or hydrates, e.g., hydrochloric, sulfonic, trichloroacetic acid salts, and the like, especially preferably the hydrochloric acid addition salts. The first named compound in the form of its monohydrochloride is also known as minocycline and the second named compound is also known in the form of its monohydrate as doxycycline hyclate. These compounds and methods for their preparation are disclosed in U.S. Pat. Nos. 3,148,212, 3,200,149 and 3,226,436.

Minocycline is a potent semisynthetic tetracycline analog with activity against a wide range of gram-positive and gram-negative organisms. When inserted directly into the infected pockets of beagle dogs according to this invention, minimum inhibitory concentrations (MIC's) can be achieved for periods up to two weeks. When compared with existing dosage forms needed to attain similar periodontal pocket fluid levels, administration of minocycline periodontal powder requires a dose several hundred-fold less than orally administered formulations.

The methods for preparation of microcapsules may be classified in four principal ways:

(1) phase separation methods including aqueous and organic phase separation processes, melt dispersion and spray drying;

(2) interfacial reactions including interfacial polymerization, in situ polymerization and chemical vapor depositions;

(3) physical methods, including fluidized bed spray coating; electrostatic coating and physical vapor deposition; and (4) solvent evaporation methods.

The distinguishing feature of phase separation microencapsulation is the initial production of a new dispersed phase containing the coating substances via some physical or chemical change. The dispersed coating phase ultimately surrounds and coats the core material which itself is also initially dispersed or dissolved in the continuous phase.

A preferred type of phase separation is disclosed in the above-identified commonly owned copending application Ser. No. 07/054,372, which is incorporated herein by reference. It is taught therein that microencapsulation is carried out by addition of a non-solvent for the coating polymer to a solution of the coating polymer which contains dispersed or dissolved core material. Volatile silicone fluids when used as hardening agents, result in residual hardening agent amounts of about 3 percent by weight or less, preferably less than about 1 percent in the microcapsules, and produce desirable results because these fluids do not permeate into the microparticles during the hardening step, and due to very low toxicity and non-flammability characteristics. The technique will be exemplified hereinafter.

In order to provide a biodegradable polymeric matrix for sustained release, it is preferable to select the polymer from poly(orthoesters) poly(alpha hydroxy butyric acid), poly(p-dioxanone) poly(l-lactide), poly(dl-lactide), polyglycolide, poly(glycolide-co-lactide), poly(glycolide-co-dl-lactide), a block polymer of polyglycolide, trimethylene carbonate and polyethylene oxide, or a mixture of any of the foregoing.

The encapsulating polymer, poly(glycolide-co-dl-lactide), which serves as the preferred sustained release delivery system for the encapsulated formulation herein is similar in structure to the absorbable polyglcolic acid and polyglycolic/polylactic acid suture materials. The polymeric carrier serves as a sustained-release delivery system for therapeutic agents, e.g., minocycline, in the new periodontal formulation and belongs to a class of polymers known as thermoplastic polyesters. These polymers undergo biodegradation through a process whereby their ester bonds are hydrolyzed to form normal metabolic compounds, lactic acid and glycolic acid.

Copolymers consisting of various ratios of lactic and glycolic acids have been studied for differences in rates of degradation. It has been found that the biodegradation rate depends on the ratio of lactic acid to glycolic acid in the copolymer, and the 50:50 copolymer degraded most rapidly.

Criteria which core materials must satisfy in order to be microencapsulated in the phase separation microencapsulation process utilizing volatile silicone fluids as the hardening agent are as follows. The core material should have low solubility in the coating non-solvent and also low solubility in the volatile silicone hardening agent. Low solubility means less than about 5 percent weight/weight; preferably less than about 1 percent and most preferably less than about 0.1 percent. Also in the case of core materials which are microencapsulated as solids or liquids dispersed in the coating solution, the concentrated coating solution phase generated upon addition of the non-solvent must wet the core phase in preference to the continuous phase. In the case of core materials which are soluble in the initial coating solution, the core material must partition into the coating phase generated upon addition of the coating non-solvent.

Thus the class of core materials which may be microencapsulated by the process of this invention is determined by the physicochemical properties of the core, coating, coating solvent and hardening agent.

Among the therapeutic agents which satisfy these criteria in general are antibacterial agents, antibiotics, antifungal agents, anti-inflammatory agents, immunosuppresive agents, immunostimulatory agents, dentinal desensitizers, odor masking agents, immune reagents, anesthetic agents, antiseptic agents, nutritional agents, antioxidants, lipopolysaccharide complexing agents, peroxides, tissue growth factors, or a mixture of any of the foregoing. Specific examples of preferred antibiotic agents include: penicillins, cephalosporins, quinolones, aminoglycoside antibiotics (gentamycin, tobramycin, kanamycin, amikacin), tetracyclines (minocycline, doxycycline, oxytetracycline, chlortetracycline, demeclocycline, methacycline), clindamycin, metronidazole and pharmaceutically acceptable salts or hydrates of the foregoing. In the copending application, Ser. No. 07/054,372, it is shown specifically that peptides meet the criteria for incorporation into microparticles by the phase separation process.

Betalactamase inhibitors may be used in combination with the penicillins. Especially preferred tetracyclines are minocycline and doxycycline, their salts and hydrates, as mentioned above.

As an added advantage in preferred systems, as the sustained release formulation specific for tetracycline antibiotics degrades after administration, as it is intended to, weak acids (lactic and glycolic) are generated. Tetracycline antibiotics such as minocycline are most stable in aqueous solutions under mildly acidic conditions. Thus, the formulation exerts a protective effect that makes it possible to deliver such drugs over an extended period of time.

The therapeutic agent of this invention is most preferably minocycline-containing microcapsules or doxycycline-containing microcapsules or other tetracycline-containing microcapsules and is administered as a dry powder which absorbs water upon administration and becomes tacky. This promotes adhesion to the tissues which form the crevicular pocket. Inactive components are polymers which biodegrade and do not require removal from the crevicular pocket.

Pharmacokinetic investigation of minocycline-containing periodontal microcapsules was undertaken to produce a dosage form that could be administered to the periodontal pocket and that would yield minocycline concentrations exceeding the MIC's (0.05–1.56 mcg/ml) for organisms associated with periodontal disease for extended periods of time. Therefore, a study to evaluate four different minocycline periodontal formulations relative to determining minocycline levels in crevicular fluid was conducted in a dog model. The study utilized beagle dogs with surgically created "chronic" intrabony periodontal defects. This model entails the extraction of the two lower fourth premolars and the induction of surgically created intrabony defects at the mesial surface of the first molars and distal surface of the third premolars. Facial, lingual interproximal bone and denuded (root planned) root surfaces comprise the surgically induced circumference of a 6–7 mm deep intrabony defect.

In sequence, the defects were created as follows: First, the lower fourth premolars were extracted, sockets were allowed to heal for one month, and dogs received a full mouth scaling and tooth cleaning. A mucoperiosteal periodontal flap procedure was then performed in each of the lower quadrants, and intrabony defects were created at the mesial surface of the first molars and distal surface of the third premolars. The bone immediately adjacent to the interproximal surfaces of the teeth was removed by a dental high-speed drill under constant water irrigation. The cementum lining of the tooth was also removed. Before replacing the periosteal flaps, a stainless steel wire was placed around the neck of the teeth, formed into a loop, and bent into the bony defect, and a piece of aluminum foil, cut to fit the defect, was placed between the wire and the tooth surface. The wires were left in place for six weeks to permit a subgingival plaque to be organized. The wires were then cut and removed, together with the aluminum foil. Dogs were monitored for an additional four weeks.

For evaluation of crevicular levels of minocycline, dogs were placed under general anesthesia, and the various formulations were administered into the periodontal pockets associated with the created defects. Formulations were administered in dry form with the aid of a special dispenser. Visual evaluation (primarily to note physical retention of material) and crevicular fluid collection were performed generally at two and 24 hours and at 4, 7, 10, 14 and 28 days after treatment. Three of the four formulations (A, B, C) were studied for only one treatment administration, while the fourth formulation (D) was studied for two treatment cycles. Samples of gingival fluid were collected on a Periotron paper strip placed at the orifice of the defect for 30 seconds. The strip was then removed, and the relative amount of fluid was determined by a Periotron 6000 instrument. Paper strips were collected in vials and frozen to −20° C. until assayed.

Strips were assayed for minocycline by a microbiological technique that involves use of the minocycline-susceptible bacterium, *Bacillus cereus*. Bacteria were seeded into nutrient agar. After pouring the agar into petri dishes and allowing the agar to harden, holes were punched into the agar, where the strip specimens were then placed. Plates were then incubated for 16–20 hours at 30° C. Zones of inhibited bacterial growth were plotted, and the quantity of minocycline present was determined by comparison with zones obtained with minocycline solutions of known concentration.

The dose of minocycline in all formulations corresponded to 1 milligram of minocycline free base per pocket. Mean crevicular fluid levels of minocycline for all four formulations were maintained above 10 mcg/ml for seven days. Formulations B and C maintained mean levels above 10 mcg/ml for ten days, while Formulation D yielded minocycline levels above 10 mcg/ml for 14 days. On the basis of this information, Formulation D was administered to dogs for a second treatment cycle, and similar results were found. See FIGS. 1–5.

Minocycline-containing microcapsules are comprised of from about 1 to about 50 parts by weight of minocycline HCl, preferably from about 5 to about 40 parts by weight and especially preferably from about 20 to about 30 parts by weight per 100 parts by weight of said microcapsules. The composition is further comprised of from about 50 to about 99 parts by weight of poly(glycolideco-dl-lactide), glycolic acid initiated, preferably from about 60 to about 95 parts by weight and especially preferably about 70 to about 80 parts by weight per 100 parts by weight of said microcapsules. The composition of the copolymer is selected so as to preferably degrade within a period of about one month or less, and also so that it rapidly hydrates upon administration to the moist environment of the cervicular pocket. Hydration causes the polymer to become tacky so that the microparticles adhere to one another and to the tissues surrounding the pocket. Adhesion to the tissues surrounding the pocket provides means for retention of the formulation in the pocket and permits delivery of the pharmaceutically active agent over periods of up to two weeks. Adhesion is necessary to prevent expulsion of the dosage form from the crevicular pocket by crevicular fluid which continuously flows from the pocket.

The microparticles may range in diameter from about 0.1 to about 1000 microns, preferably from about 10 to about 200 microns and especially preferably from about 30 to about 120 microns, depending on the procedure employed.

Minocycline exists as solid particles about five microns or less in diameter distributed throughout the interior of the microparticles.

The microparticle formulation provides significant advances over other formulations designed for the treatment of periodontal disease. The inactive ingredient should be biodegradable so that it is not necessary to remove the formulation from the pocket after the drug has been released. Further, the quantity of polymer present in the periodontal pocket is so small and the degradation rate sufficiently slow that the quantity of acid produced does not adversely affect the pocket tissues.

The therapeutic-agent-containing periodontal microcapsules is preferably prepared by a phase separation microencapsulation which comprises:

(1) dispersing the active ingredient in a solution of the encapsulating polymer, for example, poly(glycolide-co-dl-lactide);

(2) adding a phase inducer to the suspension to cause the polymer to separate out in the form of small solvent-polymer droplets (coacervate) which adhere to the therapeutic agent phase;

(3) adding the above mixture to a hardening solvent which extracts the polymer solvent from the dispersed solvent-polymer-therapeutic agent phase to yield solid microparticles;

(4) recovering the therapeutic agent-containing microparticle, e.g., by filtration of the suspension through a screen; and (5) drying the therapeutic-agent-containing microparticle, e.g. by vacuum drying techniques.

Preferably, the hardening agent added is a volatile silicone.

Figure 7:
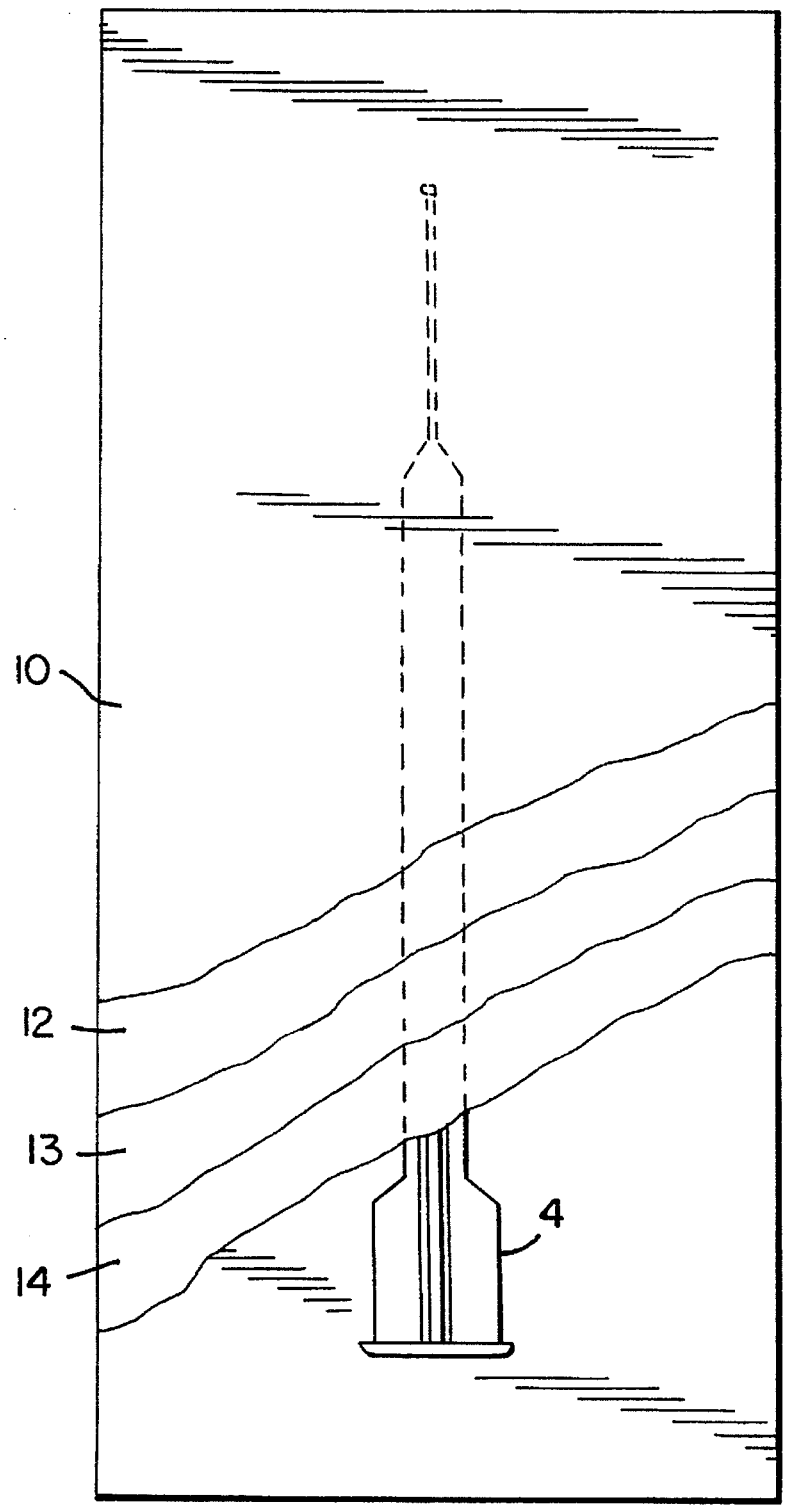
FIG. 7 is a schematic drawing of an aluminum pouch according to the invention.

The microparticles may be packaged in a dispenser. The dispenser is preferably enclosed in a moisture impermeable package, for example, a heat sealed, aluminum foil laminate pouch to prevent degradation of the formulation by moisture. The apparatus is preferably enclosed in a sterilizable package which comprises an aluminum laminate pouch, said aluminum laminate pouch comprising a heat sealable construction having a first, outer, layer of polyester, a second layer of polyethylene, a third layer of aluminum foil and a fourth, inner layer of ethyleneacrylic acid copolymer. As seen in FIG. 7, the aluminum laminate pouch has an first outer layer of polyester 10, a second layer of polyethylene 12, a third layer of aluminum foil 13 and a fourth, inner layer of ethyleneacrylic acid copolymer 14.

Figure 6A:
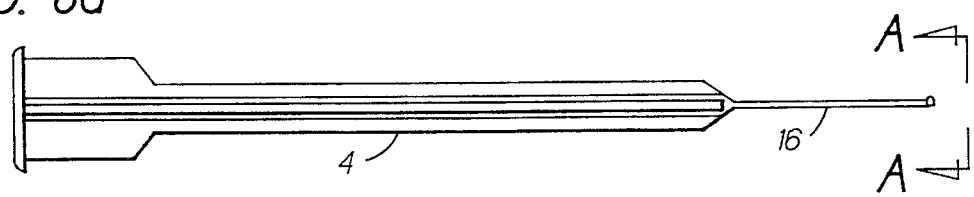
FIGS. 6(a–d) illustrates, in longitudinal cross section, a dispensing apparatus for administration of drug microparticles of the therapeutic agent directly to the periodontal cavity in accordance with this invetion.
Figure 6B:
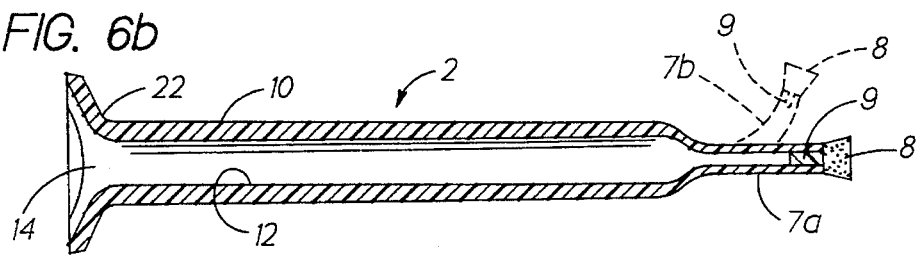
Figure 6C:
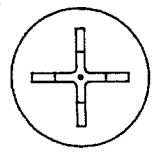
Figure 6D:
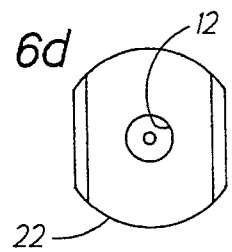

A preferred apparatus for dispensing the oral compositions of this invention to the periodontal pocket of a patient in need of such treatment is shown in FIGS. 6a–6d. Container 2 comprises barrel 10 and inner wall 12 defining a hollow area. The barrel is open at 14 and includes a finger-engaging flange 22 of the type commonly seen in syringes as shown in FIG. 6d. The barrel terminates in a tip which can be straight 7a or preferably curved to facilitate manipulation 7b. An amount of medicament 9 comprising the composition of this invention is placed in the tip, the open end of which can be closed with a cap 8, e.g., of rubber. To dispense the contents of the container, a plunger rod 4, FIG. 6a, is placed into the opening 14 with solid tip 16 partially inserted into the delivery tip 7a or 7b. The plunger rod can be of any suitable configuration, but the ribbed cross section design shown in FIGS. 6a and 6c provides good mechanical strength and light weight.

The dispenser can be made preferably from a resin selected from polypropylene, polypropylene copolymer, polypropylene random copolymer, high-density polyethylene, or a combination of any of the foregoing. These are, in general, radiation sterilizable or can be rendered sterilizable by methods known in the art. With tetracyclines, the sustained release composition of this invention comprises at least an effective or therapeutic amount and, in dosage unit form may, for example, contain from about 0.25 to about 10 mg of the tetracycline compound, for example, minocycline hydrochloride. Optionally, the dispenser may be provided with a reservoir or several reservoirs containing larger quantities of the microparticles.

The microparticles may be provided in sterile form by aseptic manufacturing techniques or by terminal sterilizing by, for example, gamma radiation after packaging.

DESCRIPTION OF THE PREFERRED EMBODIMENTS

The invention will be more fully described by the following Examples.

EXAMPLE 1

A 5 percent by solution of poly(glycolide-co-dl-lactide) glycolic acid initiated polymer, inherent viscosity 0.11 dl/g, was prepared in methylene chloride. The polymer solution is filtered through a solvent resistant filter having pore openings of 0.2 microns. 6.2 grams of milled minocycline hydrochloride is added to 300 g of polymer solution and dispersed with a high shear mixer. The dispersion is transferred to a microencapsulation vessel comprising a reactor fitted with a impeller-type, variable speed agitator and a valve for draining liquid from the bottom of the vessel. The dispersion is stirred and 300 g of polydimethylsiloxane (Dow-Corning Silicone 360 Medical Fluid), 350 centistokes viscosity, is added during about 3 minutes and stirring is continued for about 2 minutes. The dispersion is transferred from the microencapsulation vessel to a hardening tank containing about 14 kg of octamethyltetrasiloxane (Dow Corning Silicone 244 Fluid). The hardening vessel is equipped with a variable speed, propeller-type agitator. Stirring is carried out for about 2 hours. The microparticle suspension is discharged through a collection screen and the hardening tank is rinsed with 1 kg of Silicone 244 Fluid and discharged through the hardening screen. The combined microparticles are dried under vacuum at a temperature of about 40° C. The dried microparticles of this invention are sieved through a number 80 screen.

EXAMPLES 2–4

The procedure of Example 1 was repeated, substituting three higher molecular weight polymers of the same kind having inherent viscosities, respectively, of 0.22, 0.31 and 0.44. Compositions in accordance with this invention were obtained.

EXAMPLE 5

If the procedure of Example 1 is repeated, substituting for the minocycline hydrochloride an equal weight of doxycycline hyclate, a composition in accordance with this invention is obtained.

EXAMPLES 6–10

Beagle dogs with surgically created "chronic" intrabony periodontal defects are prepared as described above. A dispenser as shown in FIG. 6 is used to administer the compositions of Example 1–4 in dry form into the periodontal pockets created in the dogs. The compositions had been sterilized by gamma radiation prior to administration.

Samples of gingival fluid are collected as described above, and analyzed. Visual evaluation and collection of the fluid are performed at 2 hours, 24 hours, 4 days, 7 days, 10 days, 14 days and 28 days. The dose is all cases corresponds to about one milligram of minocycline (free base) per pocket. The strips were assayed for minocycline by bioassay with *Bacillus cereus*. The mean crevicular fluid levels of minocycline are plotted versus time in FIGS. 1–5. The compostion of FIG. 4 (Formulation D) was used in a second cycle, FIG. 5. Example 1 maintained mean minocycline levels above 10 mcg/ml for seven days—10 mcg/ml is a therapeutic level. Examples 2 and 3 maintained such therapeutic levels for ten days. Example 4 maintained such therapeutic levels for fourteen days and maintained such levels for fourteen days on a second cycle.

EXAMPLE 11

If the procedure of Examples 6–10 is repeated substituing the doxycycline composition of Example 5, sustained therapeutic levels of doxycycline in the crevicular fluid will be maintained.

The above-mentioned patents, applications and publications are incorporated herein by reference.

Many variations of this invention will occur to those skilled in the art in light of the above, detailed description. For example, instead of minocycline and doxycycline, steroids, non-steroidal anti-inflammatory agents or tissue growth factors can be used. Instead of silicone oil as a non-solvent, mineral oil or peanut oil can be used to make the microparticles. Instead of methylene chlorides other encapsulating polymer solvents such as ethyl acelate, methyl acelate, ethyl formate, or methyl formate may be used.

Microencapsulation processes other than phase separation may be used.

Other biodegradable enconnecting polymers which become tacky upon contact under water may be used. All such obvious variations are within the full intended scope of the appended claims.

We claim:

1. Apparatus for dispensing an oral composition for alleviating dental diseases by local administration of a therapeutic agent to the periodontal pocket of a patient in need of such treatment, said apparatus comprising:
   (1) a container having barrel means ending in a hollow delivery tip outlet means adapted to fit the periodontal pocket between the patient's gum and teeth;
   (2) plunger means to translate an externally applied force onto dry therapeutic agent containing microparticles contained within the outlet means so as to dispense them through said outlet means tip into said periodontal pocket said plunger means comprising a rod with a solid tip which is partially inserted into said outlet means; and in said outlet means, (3) said dry microparticles comprising:
  (i) an effective amount of at least one therapeutic agent dispersed in a dry matrix comprising a biocompatible and biodegradable polymer.

2. An apparatus as defined in claim 1 which also includes:
(4) a disposable closure on the open end of said outlet means to maintain the integrity of the contents.

3. An apparatus as defined in claim 1 enclosed in a sterilizable package.

4. An apparatus as defined in claim 3 wherein said sterilizable package comprises an aluminum-laminate pouch.

5. An apparatus as defined in claim 1 which comprises a polymer selected from the group consisting of radiation sterilizable olefin homopolymers, radiation sterilizable copolymers and mixtures thereof.

6. An apparatus as defined in claim 5 wherein said olefin homopolymer or copolymer comprises a polymer selected from the group consisting of polyethylene and polypropylene.

7. An apparatus as defined in claim 1 wherein the dental diseases to be treated are periodontal diseases.

8. An apparatus as defined in claim 1 wherein said therapeutic agent is selected from the group consisting of an antibacterial, an antibiotic, an antifungal agent, an anti-inflammatory agent, an immunosuppressive agent, an immunostimulatory agent, a dentinal desensitizer, an odor masking agent, an immune reagent, an anesthetic, an antiseptic, a nutritional agent, an antioxidant, a lipopolysaccharide complexing agent, a peroxide, a tissue growth factor or a mixture of any of the foregoing.

9. An apparatus as defined in claim 1 wherein said therapeutic agent has antibiotic activity.

10. An apparatus as defined in claim 9 wherein said therapeutic agent comprises an antibiotic selected from the group consisting of a tetracycline, a pharmaceutically acceptable salt of a tetracycline, hydrates of a tetracycline and hydrates of a pharmaceutically acceptable salt of a tetracycline.

11. An apparatus as defined in claim 10 wherein said therapeutic agent comprises a tetracycline selected from the group consisting of doxycycline a pharmaceutically acceptable salt of doxycycline, hydrates of doxycycline and hydrates of a pharmaceutically acceptable salt of doxycycline.

12. An apparatus as defined in claim 10 wherein said therapeutic agent comprises a tetracycline selected from the group consisting of minocycline, a pharmaceutically acceptable salt of minocycline, hydrates of minocycline and hydrates of a pharmaceutically acceptable salt of minocycline.

13. An apparatus as defined in claim 10 wherein said therapeutic agent comprises from about 5 to about 40 parts by weight per 100 parts by weight of said microparticles.

14. An apparatus as defined in claim 1 wherein said polymer is selected from the group consisting of polyglycolide, poly(l-lactide), poly(dl) lactide, poly (glycolide-co-dl lactide), poly (alpha hydroxybutyric acid, poly(orthoesters), poly (p-dioxanone) and mixtures of any of the foregoing.

15. An apparatus as defined in claim 14 wherein said biocompatible and biodegradable polymer comprises poly(glycolide-co-dl-lactide).

16. An apparatus as defined in claim 14 wherein said biocompatible and biodegradable polymer comprises a block copolymer of polyglycolide, trimethylene carbonate and polyethylene oxide.

17. An apparatus as defined in claim 1 wherein said polymer becomes tacky upon contact with water.

18. An apparatus as defined in claim 1 wherein said microparticles have a diameter of from about 0.1 to about 1000 microns.

19. An apparatus as defined in claim 18 wherein said microparticles have a diameter of from about 10 to about 200 microns.

20. An apparatus as defined in claim 19 wherein said microparticles have a diameter of from about 30 to about 120 microns.

21. An apparatus as defined in claim 1 wherein said therapeutic agent comprises from about 0.00001 to about 50 parts by weight per 100 parts by weight of said microparticles.

22. An apparatus as defined in claim 21 wherein said therapeutic agent comprises from about 5 to about 40 parts by weight per 100 parts by weight of said microparticles.

23. An apparatus as defined in claim 1 wherein the container and the means to translate an externally applied force onto said microparticles comprises a radiation sterilizable polymer selected from the group consisting of olefin homopolymers, olefin copolymers and mixtures thereof.

24. An apparatus as defined in claim 23 wherein said olefin homopolymer or copolymer comprises a polymer selected from the group consisting of polyethylene and polypropylene.

25. Apparatus for dispensing a solid oral composition for alleviating dental diseases by local administration of a therapeutic agent to the periodontal pocket of a patient in need of such treatment, said apparatus comprising:

(1) a container having a barrel means ending in outlet means having a uniform interior cross-section as compared to said to said barrel means, and a hollow delivery tip adapted to fit into the periodontal pocket between the patient's gum and teeth; and (2) plunger means to translate an externally applied force onto a solid oral composition of microparticles, contained only within said outlet means, so as to dispense said solid oral composition of microparticles through said hollow delivery tip into said periodontal pocket, said plunger means comprising a rod with a solid tip which has a uniform cross-section which fits into said uniform outlet means and is partially inserted into said uniform interior outlet means.

26. An apparatus as defined in claim 25 which also includes a disposable closure on the open end of said outlet means to maintain the integrity of the contents.

27. An apparatus as defined in claim 25 enclosed in a sterilizable package.

28. An apparatus as defined in claim 27 wherein said sterilizable package comprises an aluminum-laminate pouch.

29. An apparatus as defined in claim 25 wherein the dental diseases to be treated are periodontal diseases.

30. An apparatus for dispensing a solid oral composition for alleviating dental diseases by local administration of a therapeutic agent to the periodontal pocket of a patient in need of such treatment, said apparatus comprising:

(1) a container having a barrel means ending in outlet means having a hollow delivery tip adapted to fit into the periodontal pocket between the patients's gum and teeth; and (2) plunger means to translate an externally applied force onto a solid oral composition contained within the outlet means so as to dispense said oral composition through said outlet means tip into said periodontal pocket said plunder means comprising a rod with a solid tip which is partially inserted into said outlet means wherein said apparatus is packaged in a sterilizable package comprising an aluminum laminate pouch wherein said aluminum-laminate pouch comprises a heat sealable construction having a first, outer, layer of polyester, a second layer of polyethylene, a third layer of aluminum foil and a fourth inner layer of ethyleneacrylic acid.

31. Apparatus for dispensing an oral composition for alleviating dental diseases by local administration of a therapeutic agent to the periodontal pocket of a patient in need of such treatment, said apparatus comprising:

(1) a container having barrel means ending in a hollow delivery tip outlet means adapted to fit the periodontal pocket between the patient's gum and teeth;

(2) plunger means to translate an externally applied force onto dry therapeutic agent containing microparticles contained within the outlet means so as to dispense them through said outlet means tip into said periodontal pocket said plunger means comprising a rod with a solid tip which is partially inserted into said outlet means; and in said outlet means, (3) said microparticles comprising:

(i) an effective amount of at least one therapeutic agent dispersed in a matrix comprising a biocompatible and biodegradable polymer;

(4) said apparatus being enclosed in a sterilizable package which comprises an aluminum laminate pouch, said aluminum laminate pouch comprises a heat sealable construction having a first, outer, layer of polyester, a second layer of polyethylene, a third layer of aluminum foil and a fourth, inner layer of ethyleneacrylic acid copolymer.

* * * * *